(12) United States Patent
Schloemer

(10) Patent No.: US 6,861,525 B2
(45) Date of Patent: Mar. 1, 2005

(54) PROCESS FOR THE PREPARATION IMIDAZO[1,2-A]PYRIDINE-3-ACETAMIDES

(75) Inventor: George C. Schloemer, Longmont, CO (US)

(73) Assignee: Scinopharm Taiwan, Ltd., Tainan (TW)

( * ) Notice: Subject to any disclaimer, the term of this patent is extended or adjusted under 35 U.S.C. 154(b) by 0 days.

(21) Appl. No.: 10/620,209

(22) Filed: Jul. 14, 2003

(65) Prior Publication Data

US 2004/0010146 A1 Jan. 15, 2004

Related U.S. Application Data

(60) Provisional application No. 60/396,278, filed on Jul. 15, 2002.

(51) Int. Cl.⁷ .............................................. C07D 471/04
(52) U.S. Cl. ........................ 546/121; 546/113; 564/160
(58) Field of Search ................................. 546/121, 113; 564/160

(56) References Cited

U.S. PATENT DOCUMENTS

| | | | |
|---|---|---|---|
| 4,794,185 A | * | 12/1988 | Rossey et al. ............... 546/121 |
| 4,808,594 A | * | 2/1989 | George et al. ............... 514/300 |
| 4,847,263 A | | 7/1989 | George et al. |
| 5,932,592 A | * | 8/1999 | Sohda et al. ................. 514/314 |

FOREIGN PATENT DOCUMENTS

| | | | |
|---|---|---|---|
| GB | 793807 | * | 4/1958 |

OTHER PUBLICATIONS

Perez et al. J. Org. Chem. 1988, 53:408–413.*

N. S. Nudelman, et al., "Insertion of Carbon Monoxide into Lithium–Nitrogen Bonds. One–Pot Synthesis of Dialkylformamides and Dialkylglyoxylamides", J. Org. Chem., 1983, 48, 133–134.

* cited by examiner

*Primary Examiner*—Evelyn Mei Huang
(74) *Attorney, Agent, or Firm*—Cohen, Pontani, Lieberman & Pavane

(57) ABSTRACT

The present invention relates to an improved synthesis of imidazo[1,2-a]pyridine-3-N,N-dialkylacetamides, including zolpidem tartrate.

8 Claims, No Drawings

PROCESS FOR THE PREPARATION IMIDAZO[1,2-A]PYRIDINE-3-ACETAMIDES

RELATED APPLICATIONS

This application claims priority from U.S. Provisional Patent Application Ser. No. 60/396,278 which was filed on Jul. 15, 2002.

BACKGROUND OF THE INVENTION

1. Field of the Invention

The present invention relates to an improved process for preparing imidazo[1,2-a]pyridine-3-N,N-dialkylacetamides.

The present invention relates to an improved synthesis of imidazo[1,2-a]pyridine-3-N,N-dialkylacetamides. The utility of compounds of this general structure is described extensively in the literature and best represented by the well known pharmaceutical, zolpidem tartrate, which is distributed commercially for sleep disorders.

2. Description of the Related Art

Almost all previously described methods of synthesis have proceeded through the initial formation of the required imidazo[1,2-a]pyridine followed by the attachment of a suitable derivative on the 3-position and subsequent conversion to the desired acetamide derivative. Thus, U.S. Pat. No. 4,794,185 describes a method of formation of compound (I), see below, via reaction of the aldehyde prepared in situ by acid hydrolysis from N,N-dimethyl-2,2-dimethoxyacetamide, isolation of the 3-substituted derivative (III), conversion of the hydroxyl group to the chloride with thionyl chloride and subsequent reduction of the chloro derivative to the imidazo[1,2-a]pyridine-3-N,N-dialkylacetamide derivative with sodium borohydride. This process suffers from the fact that it is difficult to obtain a suitable hydrolysis product of N,N-dimethyl-2,2-dimethoxyacetamide in situ and thus the reaction can not be taken to completion. Also the procedure is very laborious and usually results in low yields. Separation of the starting imidazo[1,2-a]pyridine from the reaction product has also proven difficult. On top of that, the formation of the chloro derivative and reduction to the acetamide with sodium borohydride produces low yields which make the product difficult to purify and the addition of sodium borohydride directly to an acidic media produces a hazard in that hydrogen gas is rapidly evolved. EP 50,563 describes a process in which 6-methyl-2-(4-methylphenyl)-imidazo[1,2-a]pyridine is reacted to form 3-(N,N-dimethylaminoethyl)-6-methyl-2-(4-methylphenyl)-imidazo[1,2-a]pyridine. This compound is then treated with methyl iodide, displaced with cyanide. The resulting cyano compound can then be converted to the desired derivative in several steps. Again this is a very laborious procedure and produces low yields.

Other potentially useful derivatives and other methods for the formation of these derivatives have been reported. U.S. Pat. No. 6,407,240 B1 describes the synthesis proceeding through the corresponding ester which can then be converted to desired compound in three steps. This procedure uses undesirable chlorinated solvents in several steps.

The highly crystalline, stable hemi-hydrate of dimethylglyoxylamide (II), see below, has been reported in GB 793,807 but the use of this compound in condensation reactions with imidazo[1,2-a]pyridine has not been demonstrated.

Thus, prior methods of preparation of (I) require many steps, occur in low yield, use toxic solvents and involve complicated procedures. Therefore, there is a need for a more economic and simpler commercial synthesis.

SUMMARY OF THE INVENTION

We have found a process for the production of imidazo[1,2-a]pyridine-3-acetamides of structural formula (I) comprising reacting the corresponding imidazo[1,2-a]pyridine with compound (II) to produce compound (III) and subsequently reacting this compound with phosphorus tribromide to produce the imidazo[1,2-a]pyridine-3-acetamide. High yields are obtained in both reactions.

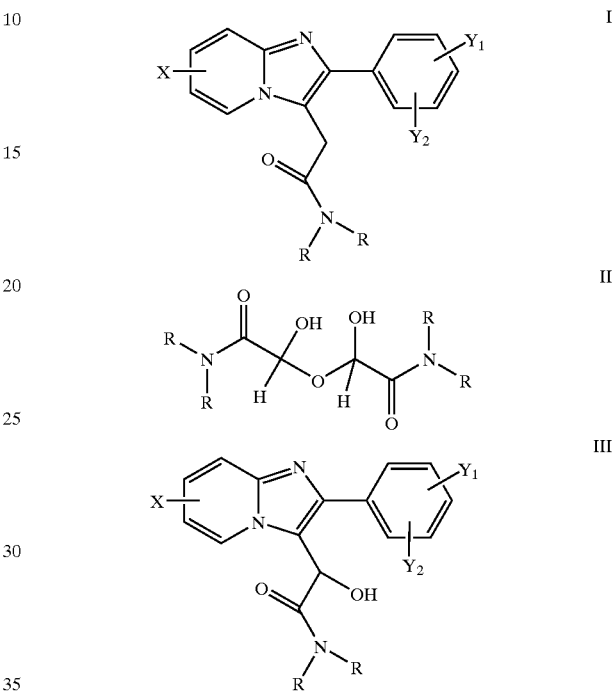

wherein X is a hydrogen or $C_{1-4}$ alkyl group and $Y_1$ and $Y_2$ are either hydrogen or $C_{1-4}$ alkyl and R is methyl or $C_{2-4}$ alkyl group. The process of the present invention is particularly useful for the preparation of the sleep disorder drug zolpidem.

The method is useful for the preparation of N,N-dialkylimidazo[1,2-a]pyridine-3-acetamide derivatives and most specifically 6-methyl-N,N-dimethyl-2-(4-methylphenyl)imidazo[1,2-a]pyridine-3-acetamide. The general process consists of reacting an imidazo[1,2-a]pyridine derivative such as 6-methyl-2-(4-methylphenyl)-imidazo[1,2-a]pyridine with the hemi-hydrate of N,N-dimethylglyoxylamide (II) in an inert solvent and subsequently reducing the derived adduct with phosphorous tribromide to form a filterable solid which upon hydrolysis produces the desired N,N-dialkylimidazo[1,2-a]pyridine-3-acetamide in good yield. When 6-methyl-2-(4-methylphenyl)imidazo[1,2-a]pyridine is employed then the desired 6-methyl-N,N-dimethyl-2-(4-methylphenyl)imidazo[1,2-a]pyridine-3-acetamide is obtained.

The first step can be carried out by simply mixing the starting materials in a solvent such as toluene, methyl isobutyl ketone (MIBK) or other solvents that are capable of azetropic removal of water and heating to remove the water of reaction. Likewise the reaction can be carried out in other solvents using a drying agent to remove water. Also in some solvents, removal of water is not necessary for effective reaction. The reaction can be carried to completion by the analysis of the mixture and the subsequent addition of more of one the starting materials as needed. The reaction can be carried out at any convenient temperature but temperatures between 40–100° C. are preferred. The pH of the reaction media can be slightly basic or slightly acidic but the addition of an acidic or basic media is not usually necessary. An interesting and advantageous aspect of the present invention is that the product formed in the first step can be carried directly into the next step of the process without isolation.

The second step of the process results through reaction of the previously derived hydroxyamide with excess phosphorous tribromide in an inert solvent. This reaction produces a salt which usually precipitates and can be collected by filtration. Surprisingly, upon hydrolysis, the desired 3-acetamide derivative is obtained directly and in good yield. The filtration and subsequent washing of the salt allows the removal of impurities and unreacted materials. Likewise, the hydrolysis of the filtered material is simplified due to the removal of the highly reactive phosphorous tribromide. Similarly the product can be isolated through direct hydrolysis of the reaction mixture.

Compound (III) can be reacted with between 1–5 equivalents of phosphorus tribromide in a variety of non-nucleophilic or non-reactive organic solvents such as chlorinated hydrocarbons, ethers such as THF, ketones, esters and aromatic hydrocarbons at temperatures 20–100 C. While many solvents can be employed, methylisobutyl ketone, THF or 1,2-dichloroethane are favorable. Methyl-isobutyl ketone is particularly favored. The product is formed as a salt and normally precipitates from the solution. The product can be hydrolyzed by addition of water directly to the reaction media and subsequent neutralization of the acid formed. The product is then extracted into the organic solvent. Preferably, the precipitated solid can be isolated directly by filtration and converted into the desired acetamide in a subsequent hydrolysis step. In the case of 6-methyl-N,N-dimethyl-2-(4-methylphenyl)imidazo[1,2-a]pyridine-3-acetamide (zolpidem) the resulting compound can be converted to the tartrate salt which is the final API form. Good yields of zolpidem can be obtained in such a manner.

The invention is also applicable to other imidazo[1,2-a]pyridine derivatives of similar structure.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

The following non-limiting examples illustrate the invention.

DETAILED DESCRIPTION OF THE PRESENTLY PREFERRED EMBODIMENTS

Example 1

6-Methyl-N,N-dimethyl-2-(4-methylphenyl)-α-hydroxyimidazo[1,2-a]pyridine-3-acetamide Slurry two grams (9.42 mmoles) of 6-methyl-2-(4-methylphenyl)imidazo[1,2-a]pyridine in 50 ml of toluene and add 1.25 grams (7.26 mmole) of N,N-dimethylglyoxylamide hemi hydrate as a solid. Heat the mixture to 85° C. and collect water through the azeotrope. A solution gradually forms and the completion of the reaction can be followed by silica gel TLC (ethyl acetate). When complete, cool the solution and add 20 ml of hexane. Filter off the white solid that forms. Evaporate the solvent and crystallize the product by addition of hot hexane to produce 2.5 grams (85%) of 6-methyl-N,N-dimethyl-2-(4-methylphenyl)-α-hydroxyimidazo[1,2-a]pyridine-3-acetamide.

A melting point of 175–177° C. is observed and the following NMR is obtained.

$^1$H-NMR (CDCl$_3$) 2.34 (s, 3H), 2.40 (s, 6H), 2.87 (s, 3H), 5.75 (s, 1H), 7.10 (d, 1H), 7.28 (d, 2H), 7.57 (d, 1H), 7.68 (d, 2H), 8.01 (s, 1H)

6-Methyl-N,N-dimethyl-2-(4-methylphenyl)imidazo[1,2-a]pyridine-3-acetamide

Dissolve 6-methyl-N,N-dimethyl-2-(4-methylphenyl)-α-hydroxyimidazo[1,2-a]pyridine-3-acetamide (0.5 grams, 1.6 mmoles) in 10 ml of 1,2-dichloroethane and add 1.2 ml of phosphorus tribromide slowly with good stirring. Heat the resulting solution for 2 hours at reflux during which time it turns orange. Cool the mixture and add 10 ml of hexane. Collect the resulting precipitate by filtration and washed with hexane. Dissolve the salt in water/ethyl acetate and sodium carbonate to produce a pH>10. Separate the layers and dry the ethyl acetate layer over sodium sulfate. Evaporate to produce a semi-solid which crystallizes when slurried in acetone to produce 0.35 grams (74%) of 6-methyl-N,N-dimethyl-2-(4-methylphenyl)imidazo[1,2-a]pyridine-3-acetamide.

$^1$H-NMR (CDCl$_3$) 2.37 (s, 3H), 2.42 (s, 3H), 2.97 (s, 3H), 3.11 (s, 3H), 4.11 (s, 2H), 7.10 (d, 1H), 7.29 (d, 2H), 7.55 (d, 2H), 7.61 (d, 1H), 8.03 (s,1H)

6-Methyl-N,N-dimethyl-2-(4-methylphenyl)imidazo[1,2-a]pyridine-3-acetamide

Dissolve 6-methyl-N,N-dimethyl-2-(4-methylphenyl)-α-hydroxyimidazo[1,2-a]pyridine-3-acetamide (1.0 gram, 3.22 mmoles) in 10 ml of warm THF and add 2.5 ml of phosphorus tribromide slowly with good stirring at 40° C. A precipitate forms immediately. Heat the mixture at reflux for 1 hour during which time it turns light orange. TLC (ethyl acetate) of the free base indicates complete conversion to the product. Cool the mixture and carefully slurry with 0.5 ml water. Collect the resulting solid by filtration and wash with THF to yield 1.05 grams after drying. Thus is obtained 6-methyl-N,N-dimethyl-2-(4-methylphenyl)imidazol[1,2-a]pyridine-3-acetamide. HBr in 86% yield.

6-Methyl-2-(4-methylphenyl)imidazo[1,2-a]pyridine to 6-Methyl-N,N-dimethyl-2-(4-methylphenyl) imidazo[1,2-a]pyridine-3-acetamide Heat 1.0 gram (4.4 mmoles) of 6-methyl-2-(4-methylphenyl)imidazo[1,2-a]pyridine in 24 ml of methyl isobutyl ketone to 60° C. and add 0.6 grams (2.72 mmoles) of N,N-dimethylglyoxylamide hemi hydrate as a solid. Continue heating for 3 hours and follow the completion of the reaction by silica gel TLC (ethyl acetate). Add 340 mg (1.55 mmoles) of N,N-dimethylglyoxylamide as a second portion and heat at 80° C. for 1.5 hours. TLC indicates complete reaction. Cool the reaction mixture to 40° C. and add 7 ml of phosphorus tribromide in two portions with good stirring. An immediate precipitate forms. Heat the mixture at 60° C. for 1 hour and cool to 25° C. Collect the solid by filtration and wash with methyl isobutyl ketone and then acetone. Slurry the solid in pH>10 water and extract with ethyl acetate. Evaporate the solvent to produce an oil which can be crystallized with the addition of a small amount of acetone. In thus manner is obtained 920 mg, 68% of 6-methyl-N,N-dimethyl-2-(4-methylphenyl)imidazo[1,2-a]pyridine-3-acetamide.

The invention is not limited by the embodiments described above which are presented as examples only but can be modified in various ways within the scope of protection defined by the appended patent claims. All references cited herein are incorporated by reference in their entirety.

What is claimed is:

1. A process for the production of a compound or a salt thereof of the formula I

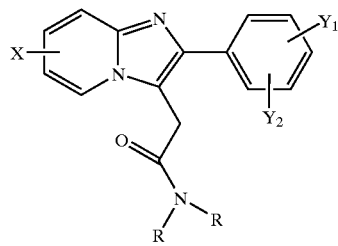

in which:
X is a hydrogen or $C_{1-4}$ alkyl group and Y1 and $Y_2$ are either hydrogen or $C_{1-4}$ alkyl and R methyl or $C_{2-4}$ alkyl group,
which comprises reacting a compound of the formula III

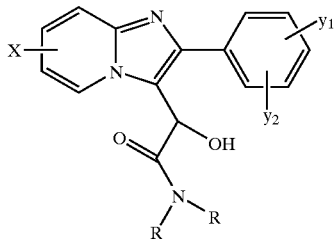

where X, $Y_1$, $Y_2$, R are defined as above, with phosphorus tribromide in a non-reactive organic solvent to produce an intermediate, and hydrolysis of the intermediate.

2. The process of claim 1 in which the organic solvent is a chlorinated hydrocarbon, ether or methyl isobutyl ketone.

3. The process of claim 1 in which X is methyl, $Y_1$ is hydrogen and $Y_2$ is methyl and R is methyl and the product is 6-methyl-N,N-dimethyl-2-(4-methylphenyl)imidazo[1,2-a]pyridine-3-acetamide.

4. A process for the formation of compound III

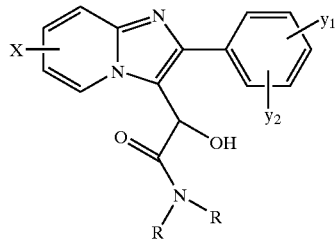

which comprises reacting a compound of formula;

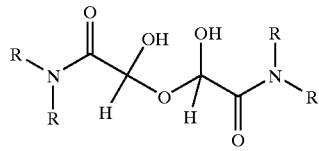

where R is methyl or $C_{2-4}$ alkyl, with an imidazo[1,2-a]pyridine of the formula;

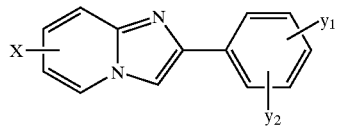

where X and $Y_1$ and $Y_2$ are either hydrogen or $C_{1-4}$ alkyl, in an organic solvent.

5. A process of claim 4 where X, $Y_1$ is methyl, $Y_2$ is hydrogen and R is methyl and the product is 6-methyl-N,N-dimethyl-2-(4-methylphenyl)-α-hydroxyimidazo[1,2-a]pyridine-3-acetamide.

6. A process of claim 4 where the organic solvent is capable of removing water as an azetrope.

7. A process of claim 4 where the pH is between 4.5 and 9.5.

8. A process of claim 4 where the organic solvent is selected from the group consisting of an alkyl hydrocarbon, aromatic hydrocarbon, chlorinated hydrocarbon, ketone, ester and ether.

* * * * *